United States Patent [19]

Lee

[11] Patent Number: 5,525,059
[45] Date of Patent: Jun. 11, 1996

[54] TECHNIQUE FOR POSITIONING DENTAL CROWNS AND INLAYS

[76] Inventor: Robert L. Lee, 22937 Grand Terrace Rd., Grand Terrace, Calif. 92324

[21] Appl. No.: 196,420

[22] Filed: Feb. 15, 1994

Related U.S. Application Data

[63] Continuation-in-part of Ser. No. 836,065, Feb. 12, 1992, Pat. No. 5,320,533.

[51] Int. Cl.⁶ .................................. A61C 3/00; A61C 5/08
[52] U.S. Cl. ............................................. 433/141; 433/218
[58] Field of Search ............................. 433/70, 71, 141, 433/146, 147, 214, 215, 152, 153, 157, 156, 162, 163; 294/1.2, 19.1, 1.1, 25

[56] References Cited

U.S. PATENT DOCUMENTS

| | | |
|---|---|---|
| 939,476 | 11/1909 | Copp .................................. 294/1.1 X |
| 1,106,815 | 8/1914 | Hopkins . |
| 1,202,698 | 10/1916 | Ford . |
| 1,809,423 | 6/1931 | Peck . |
| 1,990,381 | 2/1935 | Ivory . |
| 2,567,794 | 9/1951 | Winett . |
| 3,285,409 | 11/1966 | Loran . |
| 3,468,031 | 9/1969 | Mumaw .............................. 433/141 X |
| 3,628,249 | 12/1971 | Wurl . |
| 3,748,741 | 7/1973 | Yerkes, Jr. . |
| 3,903,605 | 9/1975 | Malmin .................................. 433/147 |
| 3,919,775 | 11/1975 | Malmin .................................. 433/32 |
| 3,974,567 | 8/1976 | Ridgeway . |
| 4,073,530 | 2/1978 | Seidler .................................. 249/19 R |
| 4,185,384 | 1/1980 | Lustig et al. .......................... 433/70 |
| 4,219,619 | 8/1980 | Zarow .................................. 433/118 |
| 4,265,618 | 5/1981 | Herskovitz et al. .................... 433/32 |
| 4,293,074 | 10/1981 | Dunsky .................................. 206/572 |
| 4,382,784 | 5/1983 | Freller .................................. 433/26 |
| 4,410,209 | 10/1983 | Trapani .................................. 294/34 |
| 4,486,177 | 12/1984 | Lekawa .................................. 433/161 |
| 4,664,628 | 5/1987 | Totaro .................................. 433/136 |
| 4,725,233 | 2/1988 | Planert .................................. 433/151 |
| 4,773,857 | 9/1988 | Herrin .................................. 433/138 |
| 4,834,654 | 5/1989 | Nussbaum .............................. 433/141 |
| 4,919,615 | 4/1990 | Croll .................................... 433/3 |
| 4,953,902 | 9/1990 | Brown .................................. 294/1.1 |

(List continued on next page.)

FOREIGN PATENT DOCUMENTS 4027955 12/1991 Germany .

OTHER PUBLICATIONS

Photocopy of "Pic-n-Stic" device manufactured by Pulpdent Corp, 1990.

*Primary Examiner*—Nicholas D. Lucchesi
*Attorney, Agent, or Firm*—Knobbe, Martens, Olson & Bear

[57] ABSTRACT

Special tools and materials are provided for the fitting and placement of artificial crowns and inlays in a patient's mouth. One version of the kit comprises test ribbons, ribbon gripping forceps, crown gripping forceps, a crown placement tool, an adhesive dispenser, expendable adhesive, an adhesive dispenser stand, an inlay/veneer placement tool, and a number of plastic or metal shims.

The inlay placement tool is fitted with hot-melt adhesive on its tip for fixed attachment of an inlay or veneer for placement in the mouth. The crown placement tool is adhered with hot melt adhesive to the biting surface of a posterior crown to be used as a crown placing device.

The ribbon forceps is used to grip a thin precut test ribbon and hold the ribbon in the patient's mouth vertically on either the front or back side of an artificial crown being placed. The crown placement tool is used to position an artificial crown in the patient's mouth onto the prepared tooth alongside the test-ribbon, whereby withdrawing the test ribbon with the ribbon forceps tests and marks the area of interproximal contact of the crown or inlay as well as the amount of pressure of the contact. The crown gripping forceps is also used to place an artificial crown for final cementation. The adhesive is not only used to place and remove an artificial crown or inlay for fitting, but is also used for the patient to bite on during cementation to keep the crown or inlay seated.

10 Claims, 10 Drawing Sheets

U.S. PATENT DOCUMENTS

| | | | |
|---|---|---|---|
| 4,975,053 | 12/1990 | Hofsess | 433/25 |
| 4,993,949 | 2/1991 | Hill | 433/141 |
| 5,035,615 | 7/1991 | Din | 433/39 |
| 5,040,981 | 8/1991 | Oliva | 433/141 |
| 5,098,292 | 3/1992 | Lazarof | 433/141 |
| 5,197,877 | 3/1993 | Andrews | 433/153 |
| 5,197,878 | 3/1993 | Lukase et al. | 433/158 |
| 5,251,943 | 10/1993 | Dalbo et al. | 294/19.1 X |
| 5,256,064 | 10/1993 | Riihimaki et al. | 433/141 |

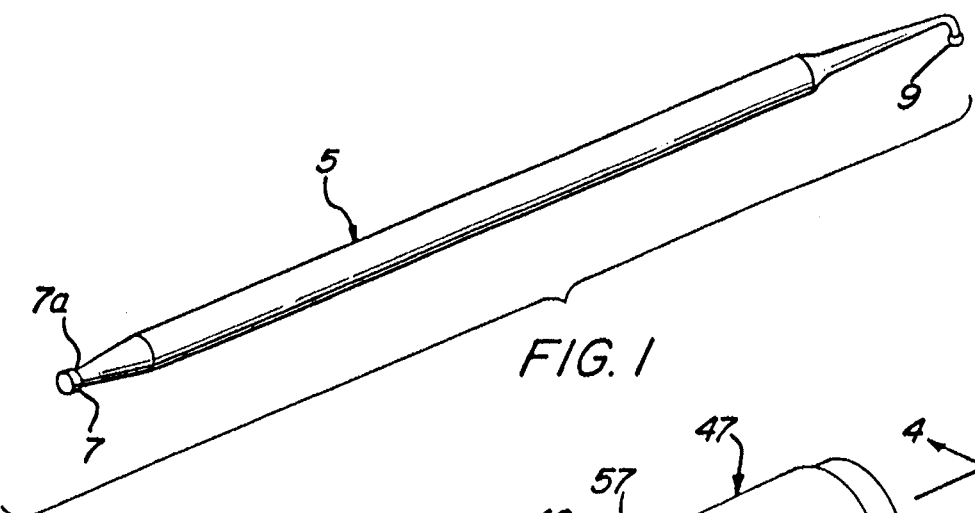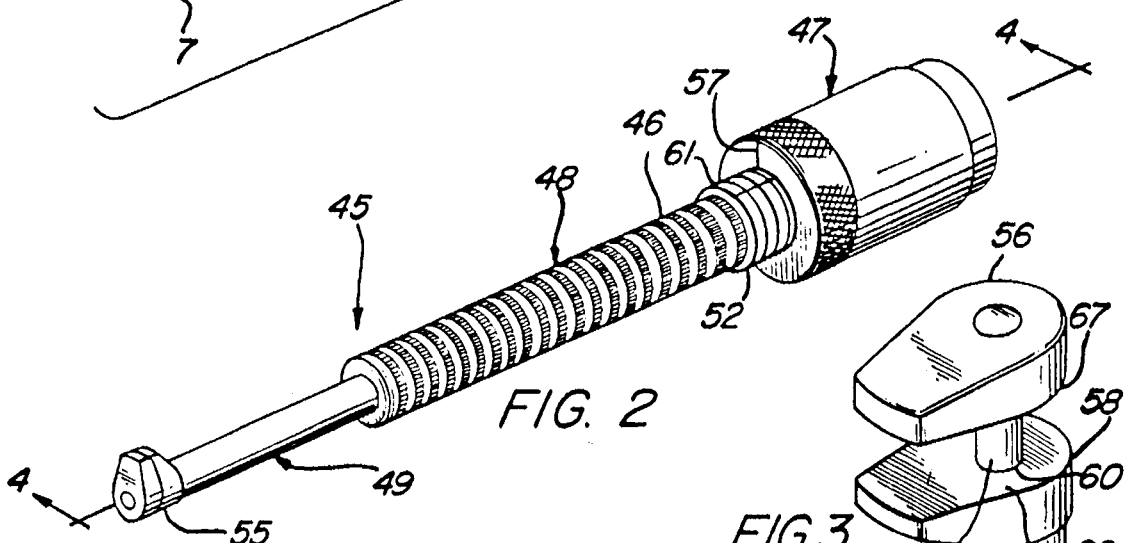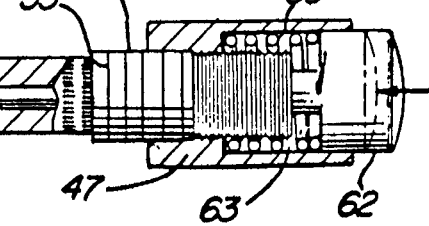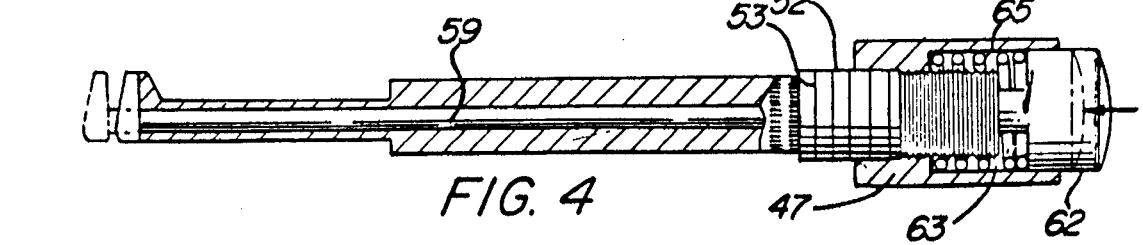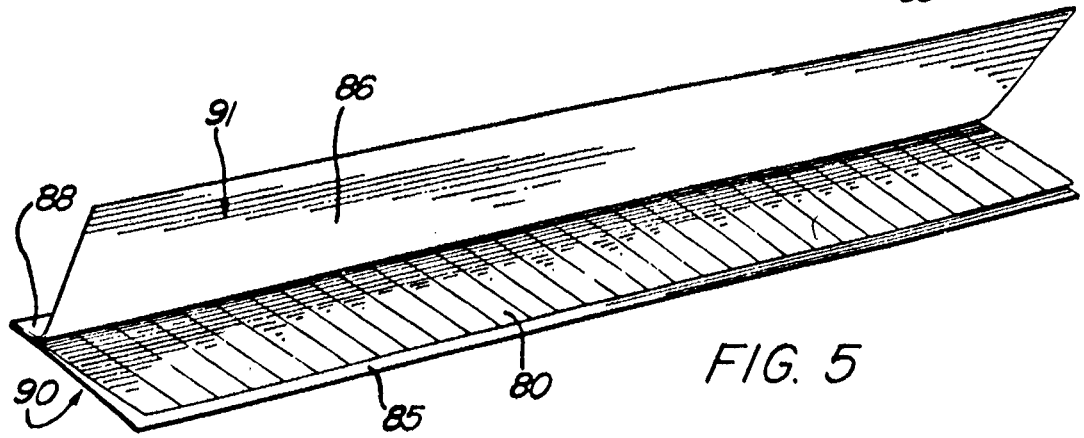

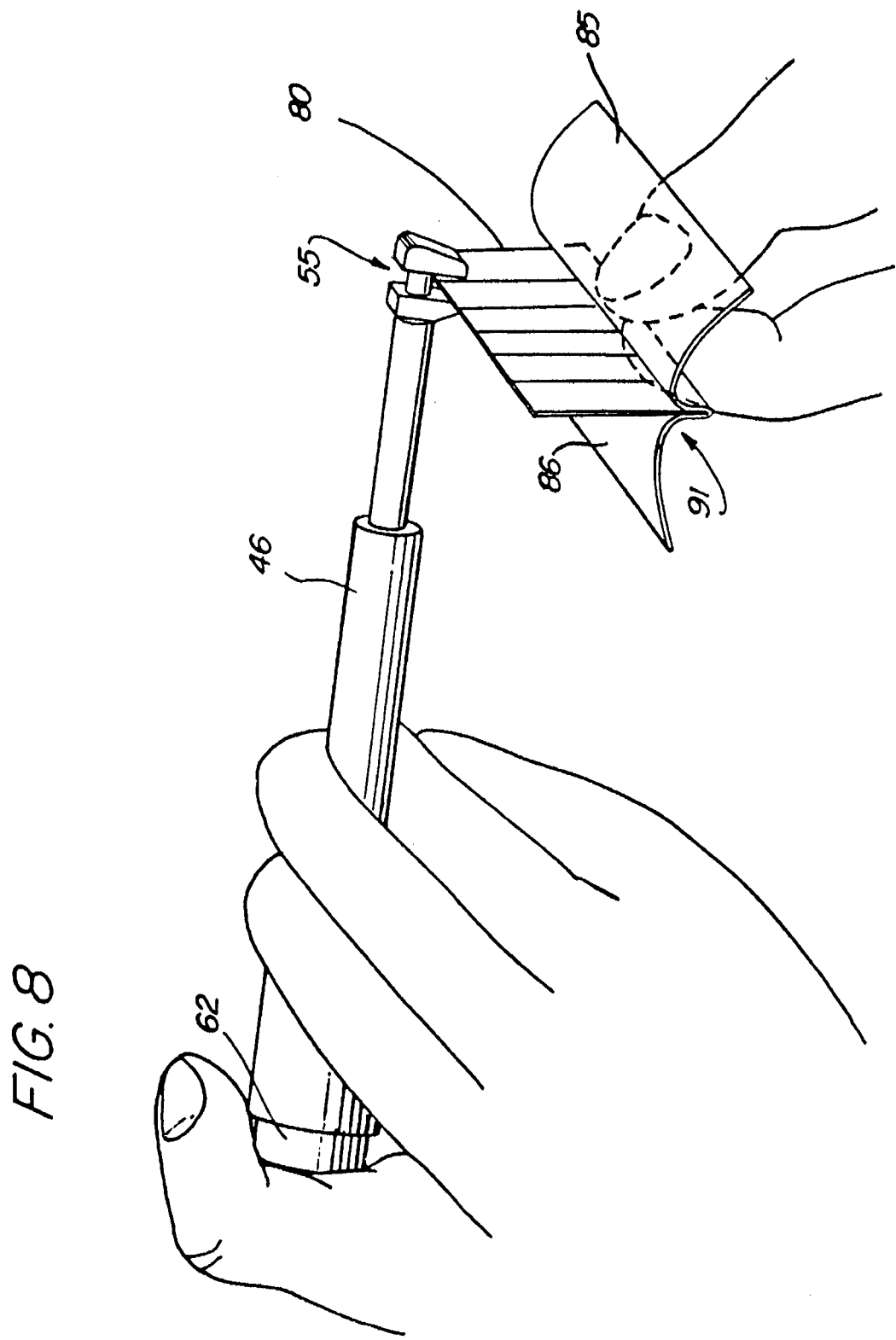

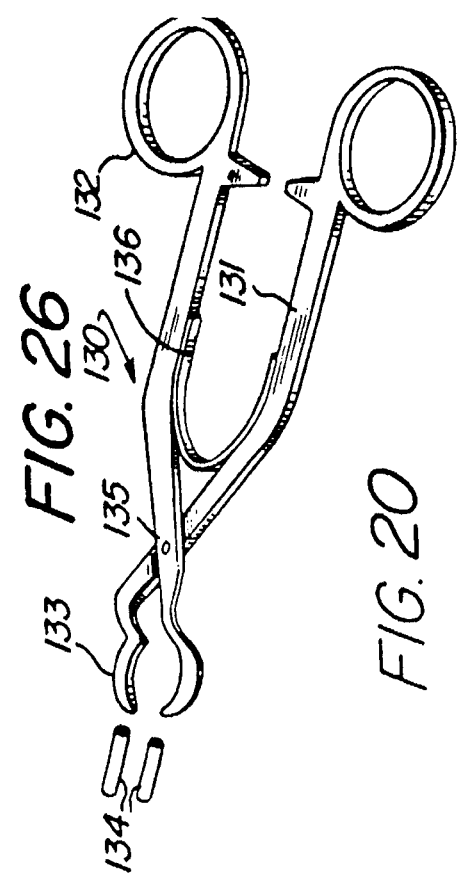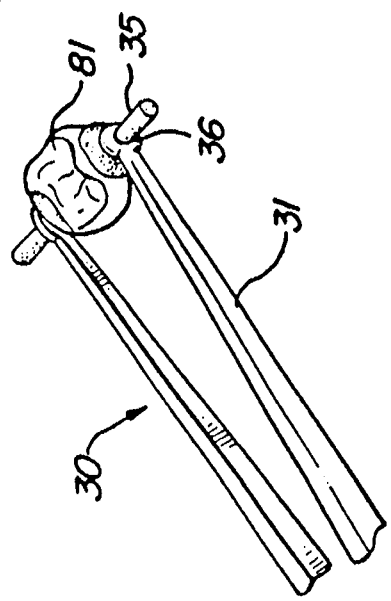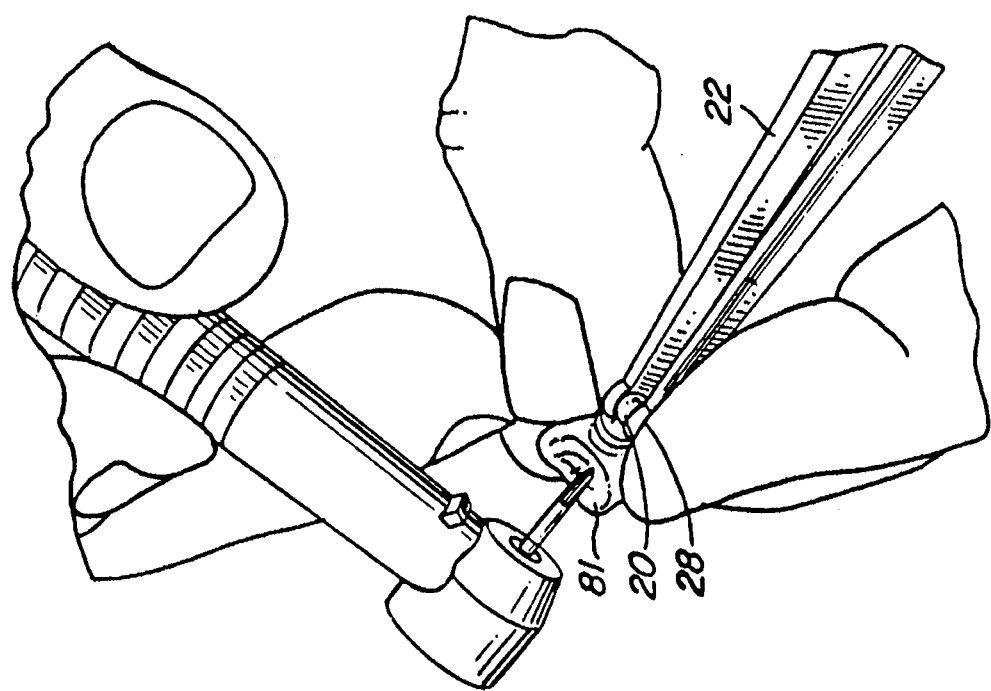

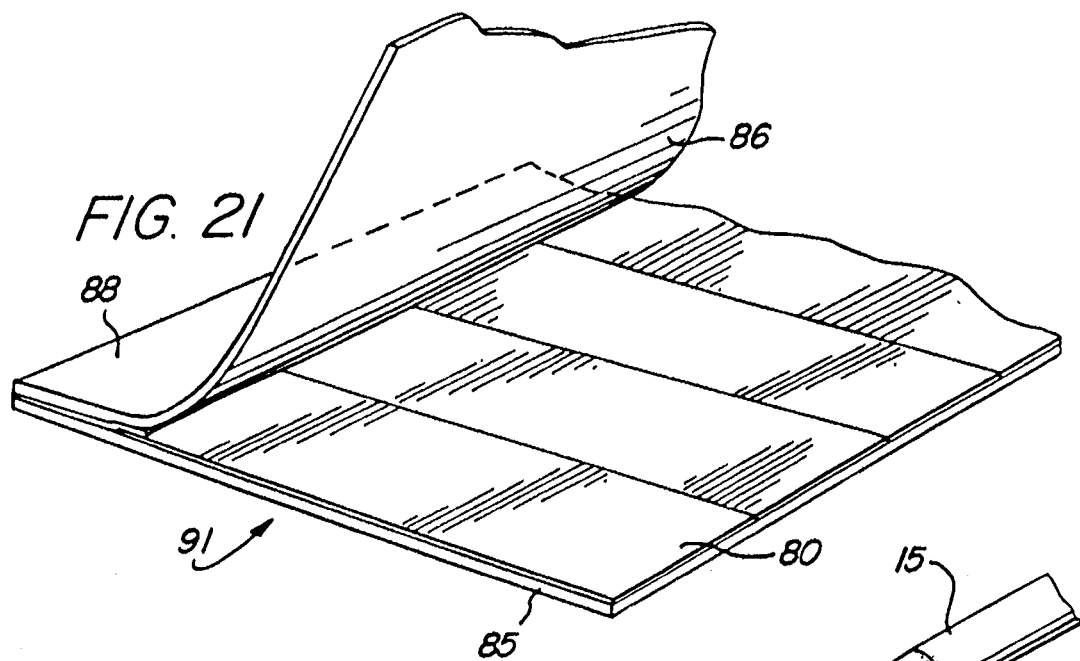
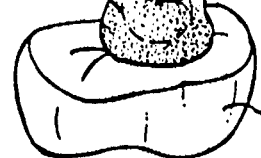
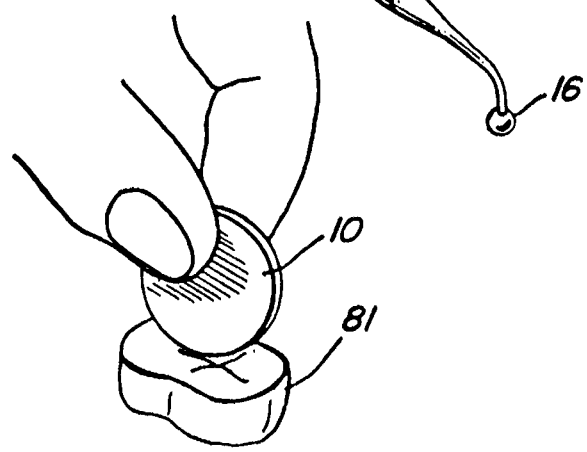

1

TECHNIQUE FOR POSITIONING DENTAL CROWNS AND INLAYS

CROSS-REFERENCE TO RELATED APPLICATIONS

This application is a continuation-in-part of Ser. No. 836,065, filed Feb. 12, 1992. Now U.S. Pat. No. 5,320,533.

FIELD OF THE INVENTION

The present invention relates generally to dental instruments and materials and methods for using them in fixed prosthodontic procedures, and more specifically to a kit containing instruments, devices and materials for facilitating the installation and fitting of artificial tooth crowns and inlays in a patient's mouth.

BACKGROUND OF THE INVENTION

Artificial dental crowns cover portions of a tooth surface and are normally fabricated away from the patient's mouth, in a lab, and then installed in the mouth. Full crowns form the entire occlusal surface of a tooth and the sides to the gum line. Partial crowns include onlays which cover the occlusal surface and sometimes portions of the sides, inlays which mainly cover central portions of the occlusal surface and may extend partially onto the sides, and veneers which mainly cover only a side surface of a tooth. For simplicity, all of these artificial elements for covering tooth surfaces will often be referred to as crowns in this document, but it should be recognized that each procedure discussed herein does not necessarily apply to all artificial crowns.

In the field of fixed prosthodontics, the proper placement and adjustment of artificial crowns has always been a cumbersome process at best because it has necessitated placing several fingers of a dentist's hand within the patient's mouth during the process. This is because as practiced now, the placement and fitting of an artificial tooth crown normally entails the dentist holding onto the crown with fingers of one hand, and then manipulating the crown in the patient's mouth to place, mark, fit and cement the crown. Often, the marking, fitting and cementing requires fingers of the other hand to be placed into the patient's mouth as well.

Often an artificial crown is fashioned with the interproximal contacts somewhat tighter than necessary and then fitted by grinding and polishing it so that it will fit in proper contact with the adjacent teeth. Even if a crown is not made intentionally in the oversized manner, the crown may fit too tightly or too loosely because of accumulative errors due to impression materials and techniques, errors in stone dies and molds, changes in the dimension of the wax patterns, investing, casting, changes during porcelain firing, and other factors. Other causes of improper contacts are because the crown was incorrectly manufactured, or because the patient's teeth have moved slightly after the impression for the crown was made.

The interproximal contacts between an artificial crown must not be too tight or the adjacent teeth, which are attached flexibly to the jaw bone by the periodontal ligament, may spread apart and move out of alignment with the other teeth, including the artificially crowned tooth. Further, too tight of an interproximal contact may prevent the patient from being able to floss between the crowned tooth and the adjacent teeth, which could lead to gum disease and tooth decay. The contact fit must also not be too loose or the ensuing space between the artificially crowned tooth and the adjacent teeth will allow food and particulate matter to collect. The ideal fit is somewhere between a tight and loose fit, with light contact between the artificial crown or inlay and the surrounding teeth desired.

Many dentists use only dental floss to check whether interproximal crown contacts are too loose or too tight. This procedure is not accurate because of the thickness of floss, which is quite gross at best. The floss may also wedge the teeth apart and make it appear that the contact is proper.

Another method of checking the interproximal contact is by placing a non-marking thin plastic strip between the interproximal contact of the artificial crown and adjacent tooth and then seating the crown and pulling on the plastic ribbon to determine if the contact is too loose or too tight. This method is more precise than using floss, but is still very subjective, difficult to accomplish, and does not mark the contact point. This method also does not tell the operator precisely how strong the pressure is on each side of the crown.

Currently, the best method for checking the interproximal crown contact involves adjusting the contact fit of the artificial crown before its final cementing. This is done by holding the crown with two fingers, one on each side, reaching into the patient's mouth, and pressing the artificial crown onto the prepared tooth. While the crown is being placed on the tooth, a piece of thin marking ribbon is slipped with tweezers between the artificial crown and the adjacent tooth in front or behind the crown being placed. The dentist seats the crown fully onto the prepared tooth and pulls on the ribbon to remove it. An estimation of the tightness of the interproximal fit is made by estimating the pulling force necessary to remove the ribbon. This estimation is very subjective and not very accurate. Further, if the contact is too great, the ribbon will often tear when being removed. When the marking ribbon is removed, it will leave a small residue on the crown at any contact point between the adjacent tooth and the artificial crown being placed.

The artificial crown is then removed with the fingers or some dental tool such as extraction forceps or a sharp probe placed under a finish line margin of the crown. Use of these tools risks great damage to the crown. After the crown has been removed it can be ground and polished down at any heavy contact point for a more precise fit. As stated above, when using this process to estimate contact, the dentist must estimate the contact pressure. The dentist may therefore grind or polish the crown incorrectly on one or more of the sides, resulting in a finished crown which still fits improperly. This fitting method is problematic in that if there is excessive crown contact on one side of the crown only, the tooth to be crowned will shift and make the crown also contact the tooth on the opposite side. The dentist cannot always tell that this is occurring and will then grind both sides of the crown, only to find that when the large side is ground down and the tooth moves back, that the other side of the crown is no longer in contact.

If the crown is too small and there is a lack of contact, the dentist must send the crown back to the laboratory to have its size increased. The lab technician does not know how much too small the crown was and will thus greatly oversize the crown. The dentist will then later have to spend significant time resizing the crown.

This process of placing, checking, and adjusting is done repeatedly until the crown or inlay is fitted to the best of the dentist's abilities. The internal fit of the crown is then checked using a standard indicator paste or powder. Once the internal fit has been adjusted and deemed satisfactory, the occluding (biting) surface is then checked and adjusted. The crown is then cemented permanently onto the prepared tooth.

Patients often experience discomfort resulting from the introduction of multiple fingers into their mouth during the process of fitting an artificial crown. The dentist often has two fingers of one hand holding the crown and two fingers of the other hand holding and placing the ribbon, all in the mouth of the patient at the same time. Further, the fitting process is made difficult because of the tight quarters and the necessity of having so many fingers in the patient's mouth. The dentist not only has a difficult time maneuvering the crown and ribbon into place, especially when the tooth being crowned is in the rear of the mouth, but the dentist's view of the mouth is often blocked. Tweezers have been used to hold the testing ribbons, however, the tweezer jaws are at the wrong angle and are not designed for holding the ribbon flat. Further, tweezers do not readily aid the dentist in estimating the contact force when pulling the ribbon from the teeth.

The process of marking an artificial crown has been further complicated by the fact that past testing ribbons have not been designed for easy use. Previously, ribbons of paper or cloth have been used, but these are very thick and difficult to fit in between the adjacent teeth and the artificial crown being placed. Paper and cloth ribbons also loose their integrity when they encounter saliva. Further, paper, cloth, and even thin-plastic ribbons often come in large sheets or rolls from which the dentist or assistant must cut or tear small individual pieces, and then grip with fingers or tweezers for placement in the mouth.

These ribbon designs are very wasteful and cumbersome. When a dentist or assistant must hold a large ribbon sheet or roll and tear or cut it, the carbon or dye on the ribbon often becomes smeared and the ribbon crumpled. The possibility of contaminating the entire sheet or roll during the cutting and marking process often dictates that the remaining ribbon on the entire sheet or roll discarded. Hand cutting of the ribbon also leads to inconsistently sized ribbons. Further, because of electrostatic forces, small pieces of the cut ribbon often cling to each other, and gloves and tools, making them difficult to handle. Lastly, cut ribbons, especially those from rolls, often tend to curl, making them difficult to place.

Another problem which arises when the crowns are fitted by hand is contamination of the crown cement by substances on the dentist's latex gloves. Materials on the gloves such as zinc stearate, talc, corn starch and other substances which the manufacturers place on the gloves to keep them from sticking to each other act as contaminants in the cement.

Further, phosphoric acid and other chemicals such as eugenol in the cementing agent can dissolve or weaken latex gloves which come into contact with them. This creates a greater risk that a breach in the gloves will occur, possibly resulting in exposure of contaminants between the dentist and patient.

Lastly, the placement of an artificial crown for cementing or fitting has been tried in another fashion. Sometimes wax, clay, or clay-like materials have been used to adhere the artificial crown to a wooden, plastic or metal stick. The artificial crown is then set onto the tooth as directed by the stick. This method is troublesome, because the wax or clay material is often very soft and not always very sticky, which makes it difficult to adjust, place, and release the crown. Often the crown prematurely releases from the material. The clay or wax material is also a contaminant and may leave deposits which can get on the internal surfaces of the crown and interfere with subsequent placements or the permanent cementing of the artificial crown.

There is a need for an effective, yet less cumbersome, means for placing and fitting artificial tooth crowns in a patient's mouth. There is also a need for testing ribbon which can be easily accessed with little waste or contamination. Lastly, there is a need for a marking, fitting and placing method which will not contaminate the artificial tooth crown or inlay cementing process.

SUMMARY OF THE INVENTION

Briefly stated, the present invention relates to an improved technique for positioning and manipulating dental crowns and inlays in a patient's mouth. Hot melt adhesive is employed to connect a dental crown, inlay, veneer or other such dental object to a tool so that the object may be positioned and manipulated without the operator having to grip the object with fingers. In one form of the invention, the hot melt adhesive is applied directly to the object, and the end of the tool is then positioned in the adhesive while it is still soft. The adhesive sets very quickly, and in a preferred form of the invention, the adhesive encloses the end of the tool so as to create a socket. The bond between the adhesive and the tool can then be broken so that the object and the socket can be moved with respect to the tool end. When utilizing a spherical tip on the tool, the object can be conveniently rotated in any direction. For a veneer to apply to a front tooth face, a tool tip having a frusto-conical shape is convenient to permit rotation of the veneer relative to the tool tip.

The characteristics of the hot melt adhesive are that it is somewhat resilient, and thus provides gripping capability. This enables the dental object to be moved to different orientations with respect to the tool tip, but the object will remain in a selected position with respect to the tip while the tool is being manipulated. The initial connection between the solidified adhesive and the tool tip must be such that the bond is readily broken with relatively modest breaking force. With some metals, such as stainless steel, the bond formed between the adhesive and the tool is such that a coating of material is employed on the tool that will make it easier to break the bond. However, after the bond has been broken, the object will not move loosely on the tool tip, but will still remain in a selected position. In a preferred form of the invention, Teflon or other such material is applied to the tool tip. This material has sufficient release or nonstick qualities that will enable the bond to be readily broken, but yet the resiliency of the solidified adhesive will adequately grip the coated tool tip.

As another approach, the tool tip may be dipped in a suitable lubricant and then wiped before the hot melt adhesive is in contact with the tool tip. This requires an additional step by the user of the technique and may result in inconsistent operator results. Consequently, the permanent release coating is preferred. Of course, a tool tip may be made of a material that has self-lubricating qualities such that no additional coating need be applied to it.

Another convenient aspect of the foregoing technique is that after a crown has been positioned for cementing, the crown placement tool may be pulled from the adhesive socket, leaving the solidified adhesive as a surface upon which the patient may bite to secure the crown during cementing. The somewhat resilient qualities of the adhesive make it a comfortable biting surface.

The adhesive may be conveniently provided by a handheld electric hot melt adhesive dispenser. Conventional hot melt adhesive rods are melted by the dispenser. The use of a kit containing dispenser, adhesive and the tools is convenient in fitting an artificial crown or inlay. The tools and materials allow for easy and exact positioning of the dental objects. The use of the kit also reduces the risk of internal crown contamination from the use of clay or wax material during cementation.

Use of the technique described allows the entire placing, fitting, and cementing process to be completed without having to place the dentist's fingers into the patient's mouth. Both the comfort to the patient and the ease in fitting removal by the dentist are increased. The use of the kit also reduces the chance that the various chemicals will contact the dentist's gloves. This reduces the possibility of contamination because of a breach in a glove.

BRIEF DESCRIPTION OF THE DRAWINGS

FIG. 1 is a perspective view of a inlay/veneer placement tool.

FIG. 2 is a perspective view of a ribbon forceps of the invention.

FIG. 3 is a perspective view of the jawed head of the ribbon forceps of FIG. 2.

FIG. 4 is a cross section of the ribbon forceps along its longitudinal axis, taken on line 4—4 of FIG. 2.

FIG. 5 is a perspective view of a three ply packet containing test ribbons.

FIG. 8 is a perspective view of a user manipulating the ribbon forceps of FIG. 2 to grip a test ribbon from a packet like that in FIG. 5.

FIG. 19 is an enlarged perspective view of a crown being ground while the ball post and ball gripping forceps remain attached to the crown.

FIG. 20 is a partial perspective view of the crown gripping forceps gripping a crown for manipulation.

FIG. 21 is an enlarged partial perspective view of the three ply packet of FIG. 5.

FIG. 23 is a perspective view of a crown placement tool.

FIG. 24 is an enlarged partial perspective view of one end of the crown placement tool in an adhesive socket created on a crown attached thereto.

FIG. 25 is a perspective view of an adhesive disc with crown attached gripped by a user for manipulation.

FIG. 26 is an exploded perspective view of another crown gripping forceps.

DETAILED DESCRIPTION OF THE INVENTION

Reference is now made to the figures wherein like parts are designated with like numerals throughout.

Referring to FIG. 1, there is shown an inlay/veneer placement tool 5. The inlay placement tool 5 is preferably a smooth shaft fashioned from stainless steel or other material which is sterilizable and will remain free from degradation. The placement tool 5 is preferably cylindrical, although it may be fashioned in any manner, including any cross sectional geometry. The placement tool 5 should be of a size such that it is easy to grip with the fingers of one hand. A cylindrical shaft with a diameter of 3/16 to 3/8 inches and a length of about 4 to 7 inches has been found to work well.

Figure 15:
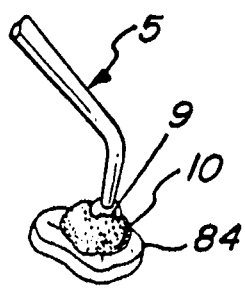
FIG. 15 is a an enlarged perspective view of the inlay end of the inlay tool of FIG. 1 being used to manipulate an inlay attached thereto.
Figure 16:
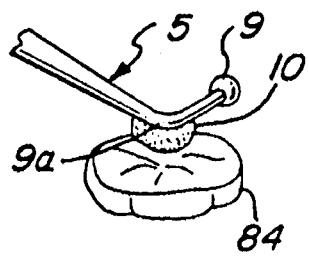
FIG. 16 is a an enlarged perspective view of the inlay end of the inlay tool of FIG. 1 being used to manipulate an inlay attached thereto.

One end of the placement tool 5 is preferably reduced in diameter and has a flat tip 7 with a frusto-conically shaped end forming a tapered throat or undercut 7a connecting to the tool handle. The other end of the placement tool 5 has a small extending end which curves away from the end and which at its tip has a small bulb 9 for the acceptance of a small amount of adhesive 10 (see FIGS. 15-17). The flat tip end 7 of the placement tool 5 is designed for use in placing facial veneers, while the smaller bulbous end 9 is designed for use in placement of posterior inlays.

Figure 12:
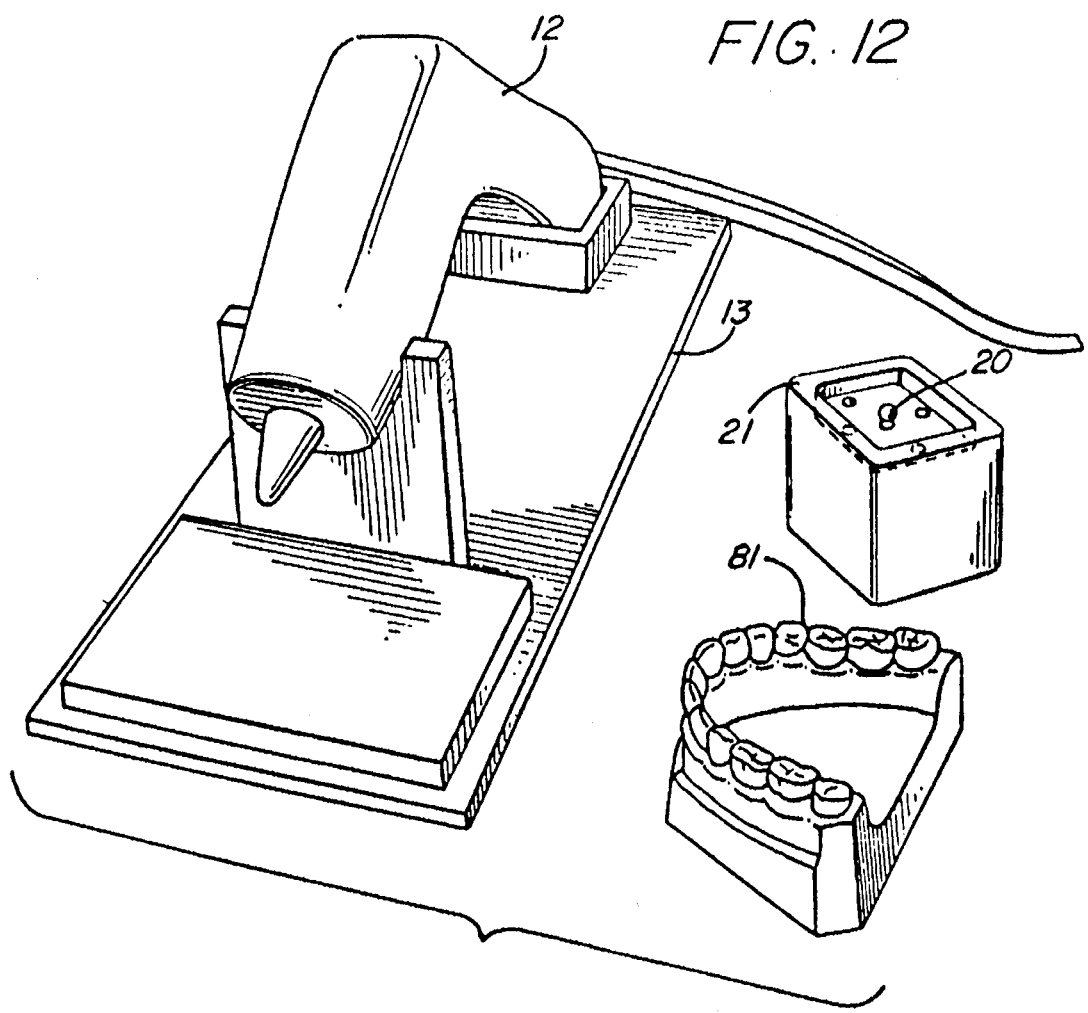
FIG. 12 is a perspective view a crown placed on a patient's dental cast, with an adhesive dispenser and stand, and with a ball post stand placed in close proximity for use.

As shown in FIG. 12, adhesive 10 is provided from a commercially available adhesive dispenser 12. The adhesive 10 is preferably a material which is solid, but somewhat resilient at room temperature, and semi-solid and very sticky at an elevated temperature. The adhesive 10 may be heated with the flame of a Bunsen burner or alcohol torch, however, preferably the electric adhesive dispenser 12 is used.

The adhesive 10 is thus preferably made of a material which melts at a predetermined elevated temperature, and is resilient but solid at room temperature and below. One suitable adhesive is that used with a glue gun, which is readily commercially available and known as hot-melt glue gun glue, and often comes in rods which are easily introduced into the adhesive dispenser 12. An example of such material is marketed by H. B. Fuller Company at 1200 Wolters Boulevard, Vadnais Heights, Minn., 55110, and further identified as HL-90181-X. It is understood that the primary component of the adhesive is ethylene vinyl acetate. The exact composition is proprietary to the Company. Other adhesive with similar characteristics are also probably suitable.

The adhesive 10 may thus be conveniently bought in rod form, and then heated in the adhesive dispenser 12 to provide a quantity of adhesive. Preferably, the dispenser 12 rests on a stand 13 which directs the discharge tip of the dispenser at a downward angle to allow easy dispensing of the melted adhesive 10. The melted adhesive 10 may be deposited on one of the ends 7 or 9 of the placement tool 5 (see FIGS. 6 and 15–17). This allows the user to customize the amount of adhesive 10 needed for the particular item that needs to be adhered.

Alternately, the adhesive 10 may be formed into an adhesive tip (not shown) which can be designed to affix an inlay or veneer to an end of the placement tool 5. The adhesive 10 may be formed into a socket so that it easily fits over one end of the placement tool 5. The material may of course, be affixed to one end of the placement tool 5 in many other manners, not limited to, but including, having a hole drilled into the end of the crown/inlay placement tool and having the adhesive tip formed such that it has a small pin for engaging the hole, or by pressing the adhesive material onto a rough crown/inlay placement tool end.

The adhesive 10, when formed into a socket or tip, can be fashioned so that such are of different sizes in order to facilitate the attachment of tooth crowns 81 or inlays of various sizes. The individual adhesive tips may be color coded by size for easy identification.

Lastly, the adhesive 10 can be formed into various shapes, such as discs or half discs, which can be heated in a small area to make it sticky so that it may be adhered to a crown. In this case, the operator merely holds onto the adhesive itself to manipulate the crown 81 or inlay (see FIG. 25).

As best seen in FIG. 23, there is provided a crown placement tool 14 comprising a cylindrical shaft 15 with a ball 16 at the distal end preferably being about 1/16 inch in diameter.

The tool 14 is preferably fashioned from stainless steel or other sturdy sterilizable material. The tool shaft 15 is preferably about 5 to 6 inches long and has a diameter of 3/16 to 3/8 inches for easy gripping with the fingers.

As is described below, a preferred method of utilizing the tool and the hot melt adhesive is to form a socket around the ball 16 on the tool 14 or on the ends of the tool 5. After the adhesive has solidified, the bond between the adhesive and the tool tip is broken by relative rotation between the adhesive and the tool tip. It may be difficult to break the bond with moderate finger pressure, when employing a stainless steel tool tip. Consequently, in a preferred form of the invention, the tip is coated with a thin layer of material, polytetrafluoroethylene, sold under the name Teflon, or other similar materials, which will release more easily than steel. This enables the bond to be broken more easily, and yet the adhesive socket grips the Teflon-coated tool tip sufficiently so that the socket attached to a crown will remain in a selected position on the tool tip.

In a current form of the product, the Teflon material is applied by first sandblasting the tool tip to roughen it slightly and then dipping the tip into heated Teflon material that is in a liquid state. The tool tip is then baked for a period of time at about 720° F. It has been found that four coatings of Teflon material, with baking in between the coatings, provides desired releasing characteristics that allow the bond to be broken and permit relative movement between the ball and the adhesive socket. Yet there is sufficient frictional gripping between the two components that they will remain in a selected position. The four coatings of Teflon material create a layer thickness in the range of 1.5 to 2 thousandths of an inch.

Applicant has obtained tool coating of this type from Truco Teflon Coating, located at 931 Claremont Avenue, Bldg. D, Westminster, Calif. 62683. That company identifies the Teflon material as T-209. Quite possibly other materials having characteristics similar to Teflon material may also be employed. It is also a possibility that the entire tool or the tool tip could be made of self-lubricating materials that would make release from the adhesive easier.

Figure 10:
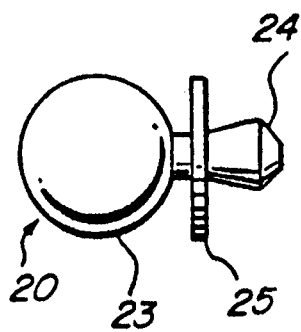
FIG. 10 is an enlarged perspective view of a ball post of the present invention.
Figure 14:
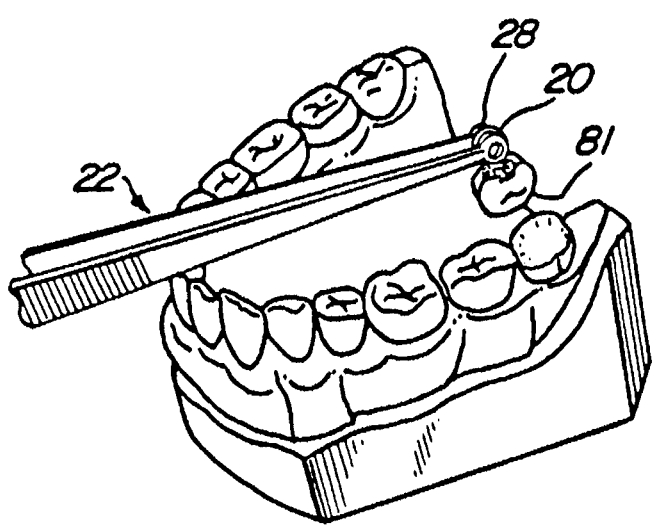
FIG. 14 is a partial perspective view of the ball gripping forceps gripping a ball post adhesively attached to a crown for manipulation.

As best seen in FIGS. 10 and 14, instead of the crown placement tool 14, there may be provided a number of ball posts 20, a ball post stand 21, and a ball gripping forceps 22.

As best seen in FIG. 10, the ball post 20 comprises a sphere 23 connected to a short post 24. The post 24 is preferably about 3/16 inches long and the sphere 23 is about 3/16 inches in diameter. A flange 25 is provided on the post 24 just below the sphere 23.

The ball gripping forceps 22 are commercially available, comprising a tweezer-like body 26 having a locking mechanism, and as shown, having ends 28 in the form of small hollow hemispheres which are sized to grip the sphere 23 of the ball post 20 (see FIG. 14).

Figure 27:
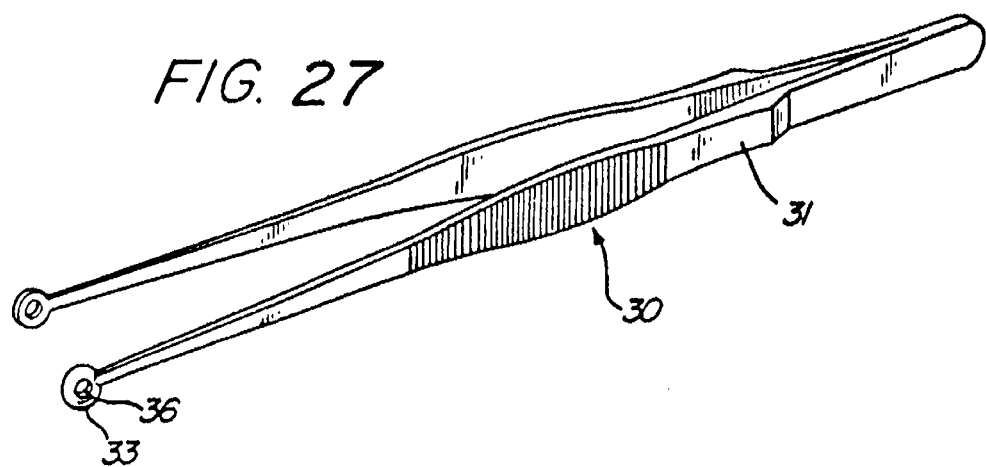
FIG. 27 is a perspective view of a crown gripping forceps.

As illustrated in FIG. 27, a pair of crown gripping forceps 30 are provided. These forceps 30 comprise a tweezer-like body 31 having a locking mechanism (not shown), and as shown, having ends 33 in the form of small concave hemispheres having replaceable resilient elements 35 shown in FIG. 20 mounted thereon. The locking mechanism may be a prestressed element which can protrude through a slot in one side of the body 31 to lock the forceps 30 together.

The ends of the forceps 33 are hemispherical and concave, having a diameter of preferably 3/16 inches. This diameter is chosen so that resilient elements 35 may easily be engaged inside the ends of the forceps. As illustrated in FIG. 20, the resilient elements 35 are mounted through a small hole 36 in each hemispherical end of the forceps 30.

Figure 11:
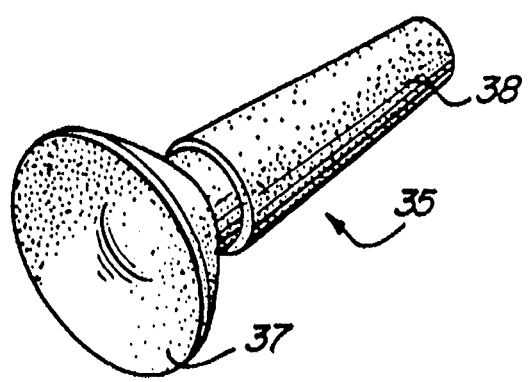
FIG. 11 is an enlarged perspective view of a suction cup of the present invention.

As best seen in FIG. 11, the resilient elements 35 have a suction cup shape with a cup area 37 and an attachment stem 38. In one form, the element 37 is hemispherical and has a diameter of about 3/16 to 1/4 inch. The stem 38 is attached to the convex side of the cup 37 and is approximately 3/8 inches long. This element 35 design, in combination with the forceps 30, allows the elements 35 to be easily replaced each time the forceps 30 are used on a new patient. Element 35 replacement may be necessary to prevent contamination or to obtain good results if the elements are damaged by use or by chemicals used in cementing or other crown fitting procedures.

An alternative form of crown removal forceps 130 is shown in FIG. 26 as including a pair of pivotally mounted handles 131 with finger holes 132 at one end and curved jaws 133 at the other end. The jaw crown engaging surfaces are curved to generally conform to the side walls of a tooth (a molar in the form illustrated), and may include serrations if desired. The jaws are also offset with respect to the handles to facilitate the pulling of posterior teeth. Resilient, easily replaceable tubes 134 fit onto the jaws 133 to facilitate gripping a crown and to protect the crown. A spring 136 between the handles on the finger hole side of the pivot 135 urges the jaws into open position. Locking lugs (not shown) have interengaging teeth to hold the jaws in gripping position. The forceps 130 is particularly useful in removing tight fitting crowns or ones that have been partially cemented but require removal.

A ribbon forceps 45, as best seen in FIG. 2, is designed to grip a test (or marking) ribbon 80 (see FIG. 8) for easy manipulation of the testing or marking ribbon inside a patient's mouth.

In the preferred embodiment, the ribbon forceps 45 has a handle 46. This handle 46 is preferably cylindrical and has three main portions: a short, large diameter spring housing 47; a hand gripping portion 48 which is somewhat smaller in diameter than the spring housing 47; and a jaw end 49 which has an even smaller diameter.

The spring housing 47 is preferably 0.75 to 1 inch in diameter and approximately 1 inch long, a portion of which is corrugated for easy gripping, and has a collar 52 which extends outwardly towards the gripping portion 48. The spring housing 47, as illustrated in FIG. 4, is threaded onto the outside of the collar 52. The collar 52 is cylindrical in shape and has annular grooves 53 etched in its outer surface at preset intervals. There is one radial alignment line 57 on the spring housing 47 which corresponds to at least one axial notch 61 on the collar 52.

The hand gripping portion 48 is preferably approximately 0.5 inch in diameter, 2.5 to 3 inches long, and is corrugated on its surface to provide a firm grip. The jaw end 49 is smooth and preferably approximately 0.1875 to 0.25 inch in diameter and 1 to 1.5 inches long. The entire length of the handle 46 is therefore about 5 to 6 inches long.

Although there are a number of methods by which test ribbons 80 may be gripped such as by use of tweezers, pliers, or fingers, preferably the gripping is done by the use of a set of jaws 55 situated on the jaw end 49 of the ribbon forceps 45. As seen in FIG. 3, the jaws 55 include a moveable jaw 56 and a fixed jaw 58 that are moveable with respect to one another. The fixed jaw 58 is preferably affixed to one end of the handle 46 while the other jaw 56 is mounted on a movable shaft 59 extending through a passage 60 in the handle 60 and the fixed jaw 58. The movable jaw 56 is fixed so that it may not rotate out of alignment with the fixed jaw 58 through the use of a key (not shown) which engages a key way (not shown) along the shaft 59.

Most importantly, it is preferred that both jaws 55 open along a line parallel to the longitudinal line of the handle 46. This is accomplished by mounting the jaws 55 so that they extend outwardly perpendicular to the handle 46.

The end of the shaft 59 terminates at a plunger 62. Mounted in this manner, the moving mechanism of the movable jaw 56 is mounted efficiently within the handle 46.

The plunger 62 is mounted partially within a chamber 63 in the spring housing 47 of the handle 46. The plunger 62 protrudes part way out of the handle 46 so that it can be manually depressed. The plunger 62 is biased outwardly by a return spring 65 mounted between one end of the plunger and the spring housing 47. The spring 65 biases the plunger 62 axially outwardly to close the jaws 55. The position in which the jaws 55 are open, and thus movable jaw 56 is moved away from the fixed jaw 58 through depression of the plunger 62 and extension of the shaft 59, is shown in FIG. 4 as indicated by the phantom lines.

The position of the spring 65 allows the user to adjust the pre-compression on it by threading the spring housing 47 along the collar 52. In this fashion, the spring 65 may be pre-compressed to a predetermined amount, and thus provide a predetermined and adjustable gripping force at the jaws 45.

The engaging face 66 of the fixed jaw 58 and the engaging face 67 of the moveable jaw 56 are primarily flat and somewhat elliptically shaped.

Figure 6:
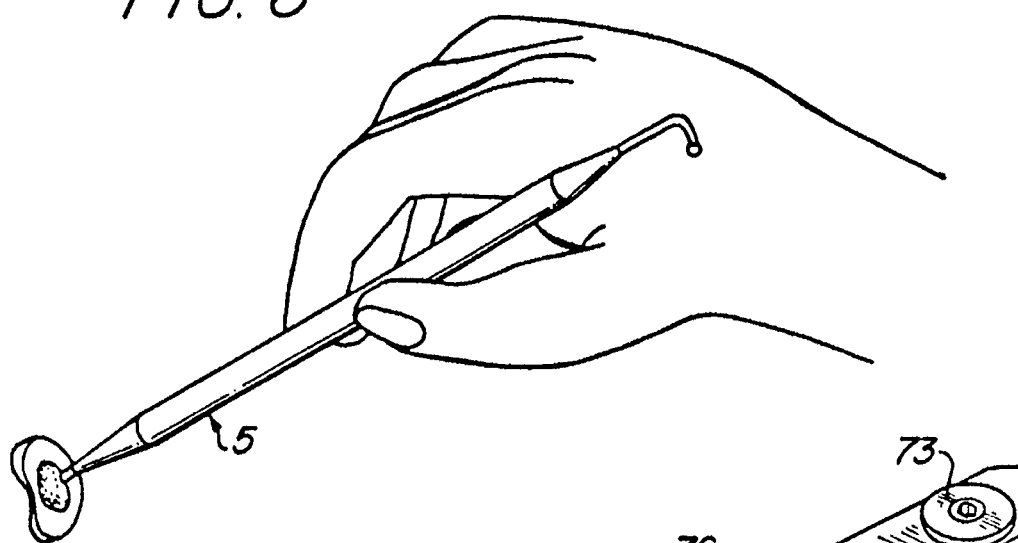
FIG. 6 is a perspective view of the inlay placement tool of FIG. 1 with adhesive on its tip and a crown attached thereto.
Figure 7:
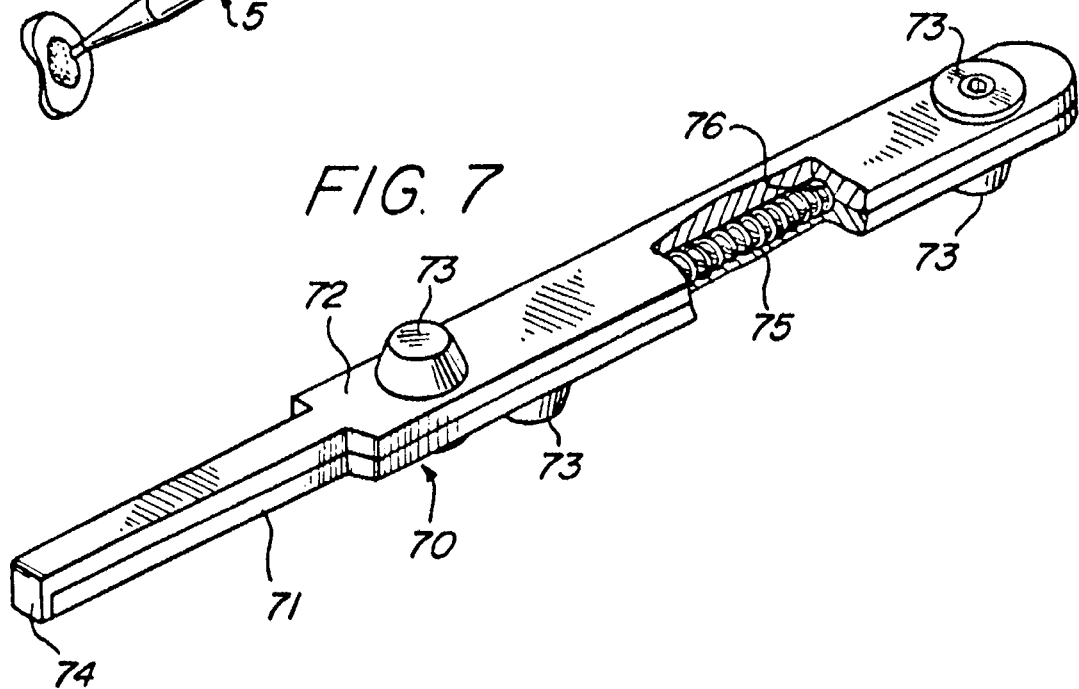
FIG. 7 is a perspective view of an alternate form of ribbon forceps.

An alternate ribbon forceps 70 is shown in FIG. 7. This ribbon forceps comprises mainly two elongated members 71, 72 and several push knobs 73. The top member 71 is a primarily rectangular and tapers to one end which has an overhang 74. The lower member 72 is preferably shaped like the top member 71, except that it has no overhang. The top and bottom members 71, 72 are connected together by two pins (not shown) which protrude through members. Knobs 73 are fixed to the ends of the pins to keep the members 71, 72 together. The pins extend through bores (not shown) in the bottom member 72 and through slots (not shown) in the top member 71. A spring 75 is mounted inside a cavity 76 inside the two members 71, 72.

A ribbon 80 may be gripped between jaws formed by the overhang 74 and the lower member 72. The jaws are opened by sliding the upper member 71 forward relative to the lower member 72. The upper member 72 slides forward as the pins move in the slots when the user pushes on the knobs 73. This action forces the jaws open causing a gap to open between the overhang 73 and the end of the lower member 72. The ribbon 80 may be inserted, and is gripped by the jaws which are closed together by the spring 75.

Referring to FIG. 5, there are shown test ribbons 80 which are used to test and mark artificial crowns or inlays for proper interproximal fitting. In the preferred embodiment, the test ribbons 80 are made of an ultra-thin carbon covered plastic, although they may be made of my type of material which will leave a mark upon the crown or inlay when in contact with the crown or inlay. Polyester plastic works well as a ribbon material due to the fact that it is very thin, in fact it is only about 0.0005 inches thick, and it is also very durable, in that it can be subjected to large pulling and gripping forces without tearing.

The test ribbon 80 material is preferably coated with a thin layer of carbon which will rub off when in contact with the tooth crown 81. The ribbon material may be coated on either one or both sides. It is advantageous to have both sides of the ribbon 80 carbon coated. Coating both sides of the ribbon 80 prevents the ribbon from curling, further, coating both sides provides a ribbon which is symmetrically identical for easy use with any tooth in the mouth.

Carbon is a good marking agent since it is not permanent, and yet it is somewhat resistant to water and is harmless to humans when ingested in small quantities. Other marking agents, such as ink, are contemplated as also acceptable.

The individual test ribbons 80 may be made by slicing a narrow strip of the ribbon, such as one 15 mm wide, perpendicular to its longitudinal axis into sections about 5 mm wide. The test ribbons 80 may have any dimension, however, these dimensions are selected so that the test ribbons fit easily between the tooth crown 81 and an adjacent tooth 83 (see FIG. 18) Further, if the ribbons 80 are to be used for marking, they must be large enough to provide an adequate marking surface. The test ribbons 80 must also have an adequate gripping length. The test ribbons 80 are thus preferably about 15 mm long, and as stated above, cut into sections about 4 mm wide.

The test ribbons 80 are preferably covered with protective strips so that the test ribbons do not rub, wrinkle or inadvertently tear. This is accomplished in the illustrated embodiment by sandwiching the test ribbons 80 between a protective backing sheet 85 and a protective cover sheet 86 which are about 1 inch wide. Adhesive, although other attachment methods are contemplated, adheres the test ribbons 80 to the protective backing sheet 85. The protective cover sheet 86 is attached with the same adhesive to the top of the test ribbons 80. The width of the adhesive area is preferably approximately 0.5 inch. The test ribbons 80 are positioned between the protective backing sheet 85 and protective cover sheet 86 and extend slightly into the adhesive preferably only approximately 1 to 2 mm. The test ribbons 80 are thus securely, but releasably affixed along one edge 88 of both of the protective sheets 85, 86. This interposition of the test ribbons 80 between the protective sheets 85, 86 thereby forms a three ply sheet 90.

The protective sheets 85, 86 may be made of paper, with the surfaces of the sheets that face the test ribbons 80 waxed to prevent rubbing of the carbon or other marking substance from the test ribbon. Further, the protective sheets 85, 86 should be very pliable so that a user may bend back the protective sheets 85, 86 to expose the test ribbons 80.

Preferably, the protective cover sheet 86 is made of a transparent material so that the user may easily see the test ribbons 80 beneath, as well as to provide enhanced aesthetic qualities. The protective backing sheet 85 may have printing, such as a name, logo, data, instructions or the like, along the edge 88 where the adhesive is applied. Because the protective cover sheet 86 and the adhesive are clear, and because the testing ribbons 80 only extend part way into the adhesive area, the user may easily see printed material on the protective backing sheet 85 as well as the test ribbons 80 inside.

The three-ply sheets 90 are preferably cut to form packets 91 containing a small number, such as five to twenty, of test or marking ribbons 80. This arrangement is preferable as it enables the user to use a few test ribbons 80 on one patient, and then dispose of the rest of the packet 91, without the corresponding waste that occurs when an entire sheet of ribbon is used and then the rest of the sheet must be thrown away after just a small amount is used on one patient. Further, when the clear protective covering sheet 86 is used, the user may easily see the number of test ribbons 80 in a packet 91, and may further individualize the number of test ribbons necessary for a patient by cutting off as few as one or two of the test ribbons from the packet.

Figure 9:
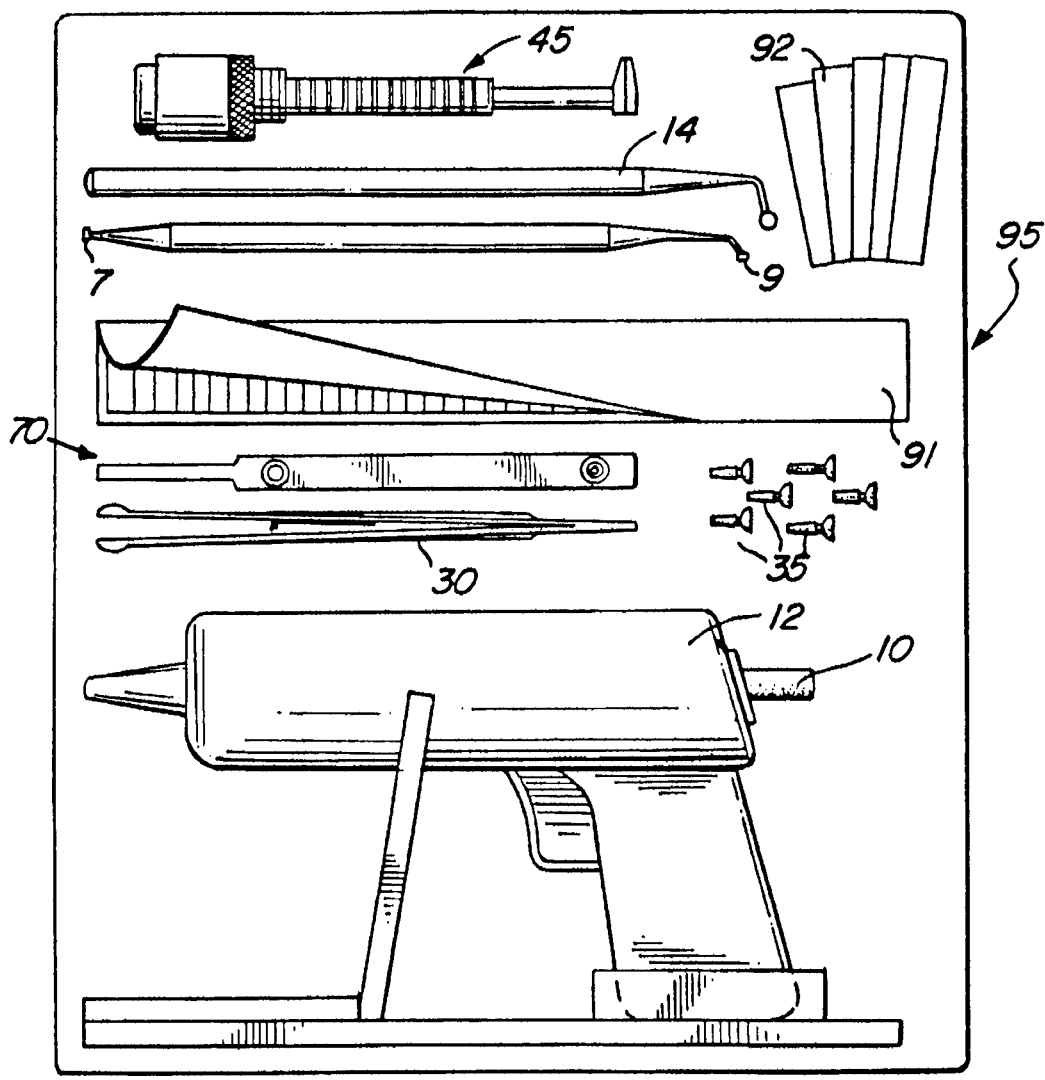
FIG. 9 is a perspective view of the fixed prosthodontic kit.

Referring to FIG. 9, there are shown a number of shims 92 for use in measuring interproximal gap or "shy contact". The shims 92 preferably comprise small pieces of plastic, metal, or other durable material. Each of the shims 92 is of a known and varying thickness. The shims 92 may be color coded according to their thickness.

As illustrated in FIG. 9, the prosthodontic tool kit 95 thus comprises: the inlay/veneer placement tool 5, the ribbon forceps 15, the crown placement tool 14 (or alternatively a number of ball posts 20, the ball post stand 21, and the ball gripping forceps 22), the crown gripping forceps 30, resilient elements 35 for the forceps 30, the adhesive dispenser 12, the dispenser stand 13, adhesive 10, a number of the three-ply sheet packets 91 containing test ribbons 80, and a number of the shims 92.

OPERATION

Figure 13:
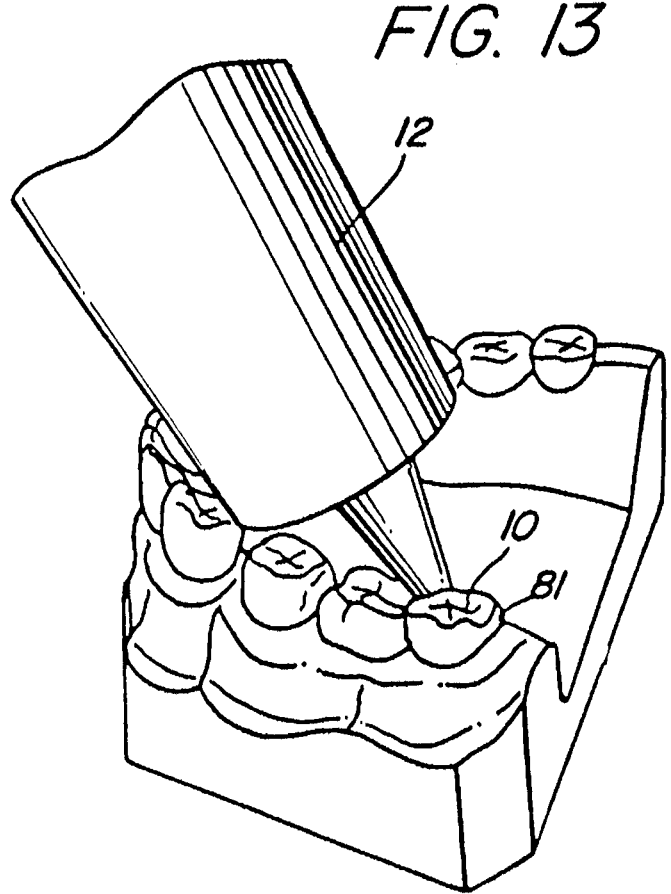
FIG. 13 is a perspective view of adhesive being dispensed from the adhesive dispenser onto a crown on the patient's dental cast.

In conjunction with FIGS. 8–21, an artificial crown fitting procedure will now be explained. The pre-prepared crown 81 is shown positioned on the patient's dental cast. The adhesive dispenser 12 is energized and adhesive 10 is heated for dispensing (see FIG. 12). A small amount of heated adhesive 10 is directed from the dispenser 12 onto the clean, dry, occlusal surface of the crown 70 (see FIG. 13). The ball end 16 of the crown placement tool 14 is then inserted into the soft adhesive 10, making sure that more than the lower half of the ball 16 is covered by the adhesive, but making sure that the adhesive does not cover any of the shaft 15 (see FIG. 24).

After the adhesive 10 has solidified, the crown 81 is twisted or pivoted about the tool 14 causing the ball 16 of the tool 14 to be released from the adhesive, creating a tight socket in the adhesive which allows the crown to pivot on the ball, or the ball to be easily rotated in the socket. The crown placement tool 14 may also be inserted or removed from the socket formed. The socket formed is quite resilient and normally very strong and thus placement and removal of crowns 81 is easily facilitated with the crown placement tool 14.

As noted above, the Teflon coating on the ball 16 of the tool facilitates the breaking of the connection between the ball and the socket. At the same time, the nature of the interengaging surfaces and the resiliency of the socket will cause the socket to remain in a selected position with respect to the ball after it has been rotated.

As an alternative to a permanent coating on the ball tip that facilitates release of the adhesive, a stainless steel tool tip can be dipped in a suitable lubricant, such as Vaseline or silicone, and then wiped before being placed in contact with the hot adhesive. Also, possibly other lubricants in liquid or powdered form could be employed. These methods, however, are believed to be less satisfactory than the permanent Teflon-type coating because of the extra steps required each time the tool is used. In addition to the time involved with such steps, the results are not uniform because of variations in operator performance.

If a large crown 81 is to be positioned, or the socket be ill-formed, it is possible that the connection between the crown placement tool 14 and the crown may be too weak. In this case the dentist may prefer to place and remove the crown 81 with the crown gripping forceps 30, as described below.

If the ball posts 20, and not the crown placement tool 14, are used, a ball post 20 is placed into the stand 21 placed near the dental cast (see FIG. 26). A small amount of adhesive 10 is directed from the dispenser 12 onto the occlusal surface of the crown 81. The operator uses the ball gripping forceps 22 in the unlocked position to pick up the ball post 20 and place the post 24 into the molten adhesive 10 on the crown 81. The advantage of the flange 25 on the ball post 20 is now apparent, as the ball gripping forceps 22 are protected from contacting the adhesive 10, and the flange 25 and post 24 aid in supporting the ball post on the crown 81. The ball post 20 is released and the adhesive 10 allowed to solidify, locking the ball post 20 in place (see FIG. 14).

Figure 17:
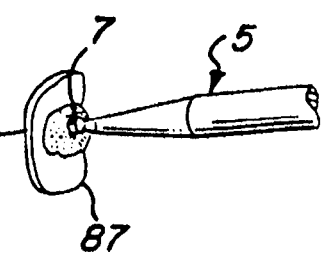
FIG. 17 is a an enlarged perspective view of the veneer end of the inlay tool of FIG. 1 being used to manipulate a veneer attached thereto.

If an inlay or veneer is to be fitted, the inlay tool 5 and not the crown gripping forceps 14 or ball post 20 are used. The adhesive 10, when heated, is effective in adhering an inlay 84 to one end of the inlay placement tool 5 in FIG. 15, and on the angled portion 9a in FIG. 16, so that the tooth inlay can be maneuvered onto a tooth with only the inlay placement tool in the patients mouth. FIG. 17 illustrates the other end 7 of the tool attached to a veneer 87 by the adhesive 10.

The operator then proceeds to prepare a test ribbon 80 for use by gripping an individual ribbon with the ribbon forceps 45 as best shown in FIG. 8. In practice, the user first lays back the protective cover and backing sheets 85, 86 so as to expose the test ribbons 80. When both of the protective sheets 85, 86 are laid back, they form a stable base which will support the test ribbons 80, which are now exposed. The user can then easily pick up the packet 91 of test ribbons 80 by the common edge with the fingers of one hand. The operator then holds the ribbon forceps 45 with the other hand and depresses the plunger 62 in to open the jaws 55. The ribbon forceps 45 are then moved into a position so that the jaws 55 straddle an individual test ribbon 80. The operator releases the plunger 62 to close the jaws 55 tightly together and grip the test ribbon 80 tightly in between. The operator moves the ribbon forceps 45 away from the three ply sheet 80 to pull the individual test ribbon 80 away from the adhesive on the three ply sheet 90.

As best seen in FIG. 21, the separation of the testing ribbon 80 from the three ply sheet 90 is facilitated by the fact that the test ribbons 80 have only a small portion (1–2 mm) of their ends attached to the adhesive. Further, since the test ribbons 80 are preferably coated with carbon when used for marking, the adhesive attaches itself to the carbon and not the underlying plastic of the pre-cut ribbons. In this manner, when the test ribbon 80 is pulled from the three ply sheet 90, the ribbon is in effect separating from and leaving behind the carbon coating at the attached end. The test ribbons 80 are therefore attached to the adhesive in a small area to both provide easy removal, and if carbon coated, this prevents a large area of the test ribbon from losing its carbon coating when removed, which would otherwise render the test ribbon unusable for marking crown contacts. The use of precut test ribbon 80 allows for removal of one individual section of ribbon merely by gripping its freed end with the ribbon forceps 45 and pulling the test ribbon away from the three-ply sheet 90, all without the need to touch the testing ribbon with hands or fingers.

Figure 18:
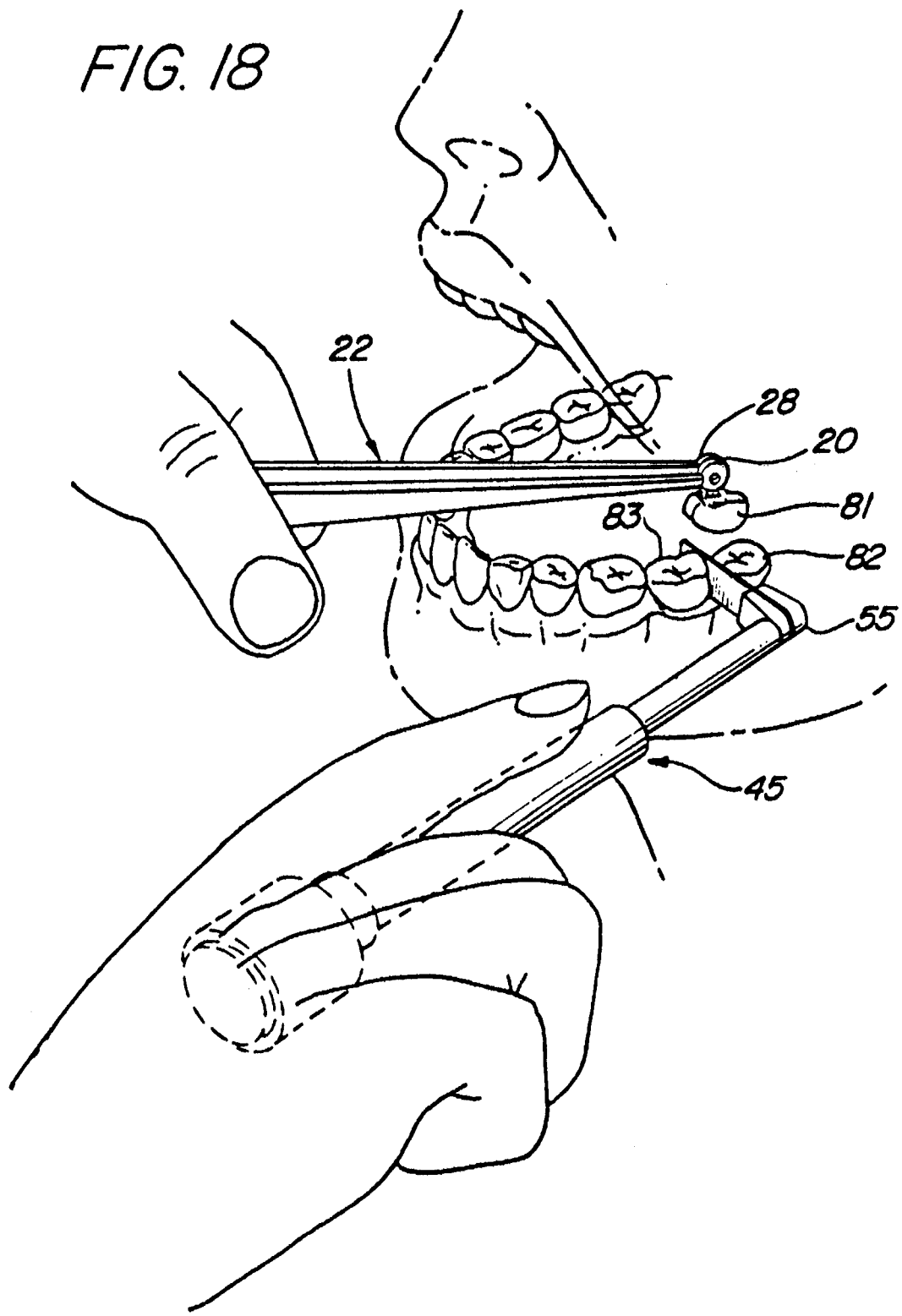
FIG. 18 is a perspective view of a test ribbon being manipulated by the ribbon forceps of FIG. 2 along with a crown being manipulated with ball gripping forceps in order to mark a tooth crown in a patient's mouth.

The marking of the tooth crown 81 is best shown in FIG. 18. The ribbon forceps 45 gripping a test ribbon 80 is guided into the mouth of the patient with the end of the ribbon forceps 45 gripping the ribbon and in a convenient location adjacent the tooth to be crowned. The ribbon forceps 45 is manipulated so that the test ribbon 80 is interposed between the tooth to be crowned 82 and one of the teeth adjacent thereto 83. The advantage of having the jaws 55 set perpendicular to the longitudinal axis of the handle 46 is best shown in this Figure. Because of the perpendicular mounting, the test ribbon 80 can easily be placed in between the adjacent tooth 83 and the tooth to be crowned 82, including those at the rear of the mouth, while the jaw clamping surfaces are generally parallel to the ribbon between the teeth and the handle 46 of the ribbon forceps 45 is positioned mainly straight out of the mouth.

Once the test ribbon 80 has been positioned, the crown placement tool 14 is used to pick up the tooth crown 81. Alternatively, the ball gripping forceps 22 may be used to pick up the tooth crown 81 by gripping a ball post 20 which has be installed. In either case the crown 81 is manipulated onto the tooth to be crowned 82 in the mouth. In either case this procedure is rendered easy because of the rotation which is allowed between the tool being used and the crown: the crown placement tool 14 rotates in the adhesive socket formed, and the ball gripping tool 22 rotates about the sphere 23 of the fixed ball post 20.

The test ribbon 80 is then pulled from between the tooth crown 81 and the adjacent tooth 83. If the contact between the tooth crown 81 and the adjacent tooth 83 is extremely tight, the operator will have difficulty in pulling the ribbon 80 and may need to lift the crown 81 from the tooth to prevent the ribbon 80 from being torn or pulled from the ribbon forceps 45. In either event there will be sufficient pressure on the ribbon 80 so that the ribbon will mark the tooth crown. The crown placement tool 14 or alternatively the ball forceps 22 is then used to remove the tooth crown 81 so that it can checked for marking, and if necessary, be ground for a lighter contact.

The exact interproximal contact pressure may be estimated through use of the spring pre-tensioning system. If a ribbon 80 does not remove easily, the operator may check the spring pre-tension on the ribbon forceps 45. If the tension is light, the spring housing 47 may be rotated to increase the spring tension and increase the jaw gripping force. This may be done until the ribbon 80 is removed from between the tooth and crown 81 and does not slip from the jaws 55. The operator can then estimate the interproximal contact by viewing the number of rings 53 exposed on the collar 52 and adding any partial rotation as evidenced by the alignment lines 57 and 61 on the housing 47 and collar.

The fitting of a tooth crown 81 may be accomplished in much the same manner using a plain test ribbon 80. In this case, however, the ribbon 80 will leave no mark upon the tooth crown 810 When these ribbons 80 are used, the dentist estimates the interproximal contact by feeling how much force is necessary to remove the test ribbon.

In the event that there is no contact between the crown 81 and the adjacent tooth 83, there will be no contact between the ribbon 80 and the adjacent tooth 83 or crown 81. In this case, the crown 80 is too small and must be fitted by enlarging it to proper size. In order to accomplish this, the amount of gap between the crown 81 and adjacent teeth 83 must be determined.

One or more of the pre-sized shims 92 are gripped in the ribbon forceps 45 and are directed next to the adjacent tooth 83. The crown 81 is then placed with the crown placement tool 14 or the ball gripping forceps 22. The operator attempts to remove the shims 92 from between the adjacent tooth 83 and crown 81 by pulling on them. If the shims 92 pull away easily, a thicker shim is used in a second trial. If the shim 92 does not pull out readily, a thinner shim is utilized. The process is repeated until a shim 92 or combination thereof fits between the adjacent tooth 83 and crown 81 snugly. The crown 81 may then be sent to a lab and adjusted by enlarging it by the amount of the shim 92 thickness. When the crown 81 is returned, it will again be tested with the test ribbons 80 to ensure a proper fit.

As best seen in FIG. 19, the crown 81 is easily ground or polished by the dentist with a drill when the crown is held securely between the fingers. This can be accomplished while the crown placement tool 14 or the ball gripping forceps 22 remain attached.

After polishing and grinding, the crown 81 may be rechecked for fitting with another ribbon 80 and then be polished or ground again if necessary.

Once the interproximal fit has been corrected, the internal fit and occlusal contact are checked. The internal portion of the crown 81 is checked by placing the crown, which has a standard paste or powder in it, onto the tooth to be crowned 82. Once again, the crown 81 is guided into the mouth with the crown placement tool 14 or, alternatively, the ball gripping forceps 22 (see FIG. 14 or 24).

The use of the crown placement tool 14 advantageously provides good contact between the crown 81 and tooth to be crowned 82. Again, this is because the ball 16 of the tool 14 may rotate in the socket created in the adhesive such that even when the tool is angled out of the mouth, and pressure directed to the crown 81 is vertically along the ball and perpendicular to the surface of the crown. This is an advantage which occurs through use of the ball posts 20 and ball gripping forceps 22 as well. This allows the operator to firmly press the crown 81 into contact with the tooth to be crowned 82 to provide good marking. Once marked, the crown 81 may be removed for grinding or polishing, and may be rechecked, as necessary.

After the internal form of the crown 81 has been checked, the occlusal surface may also be checked. To accomplish this, the operator wets the crown 81 with cool water to release the adhesive, and thus the ball post 20, if being used, from the crown 81. The crown 81 is cleaned and dried and replaced on the patient's dental cast.

As shown in FIG. 20, the crown 81 is then removed from the cast by picking it up using the crown gripping forceps 30, one suction cup 35 pressed against the lingual and one cup pressed against the buccal side of the crown. The forceps 30 are locked to secure the crown 81 in the forceps 30.

The dentist then directs the crown 81 onto the tooth to be crowned 82 as directed by the crown gripping forceps 30. Once in place, the forceps 30 are unlocked and the crown 81 released. The occlusal contact may then be adjusted and checked as necessary. Once checked, the crown 81 is removed by again gripping it with the forceps 30 or the forceps 130.

Some dentists prefer to not check the occlusal contact until after the crown 81 has been cemented into place. In this case, the above step is omitted, and the dentist proceeds directly to the next step: cementing. In this situation, the dentist uses the crown placement tool 14 to place the crown 81 for cementing. Once placed, the tool 14 may be removed and the adhesive 10 allowed to remain on the crown 81. Alternatively, if the dentist was using the ball post 20, the ball gripping forceps 22 are used to place the crown for cementing and the forceps 22 are used to removed the ball post 20 from the adhesive 10 which remains on the tooth. In either case, no additional adhesive need be added and the patient may bite down on the remaining adhesive 10 to secure the crown 81 while the cement hardens.

If the dentist checked the occlusal surface before cementation, all adhesive 10 will have been cleaned from the surface of the crown 81, and thus the dentist may apply a moderate amount of adhesive 10 onto the occlusal surface of the crown 81. The crown 81 is then picked up with the crown gripping forceps 30. The artificial tooth crown 81 is filled internally with cement and directed onto the tooth to be crowned 82 as guided by the forceps 30. Once the tooth crown 81 is placed on the tooth to be crowned 82 the forceps 30 are removed from the patient's mouth. The patient then bites down onto the solidified adhesive 10 on the tooth crown 81.

After the cement has hardened, the adhesive 10 and any excessive cementing agent is easily removed from the artificial crown 81 by spraying it with cool water. The cement or adhesive may then be flaked off with any number of standard dental tools.

A tooth inlay is cemented in much the same fashion, however, the inlay/veneer placement tool 5 is used. The inlay is guided into place with the placement tool 5 and cemented into place. The placement tool 5 is twisted and removed from the adhesive 10, which the patient bites down upon to maintain cementing position. The shape of the veneer end 7 of the tool 5 aids in the tool removal process, as its cylindrical shape allows the dentist to rotate the tool free in the adhesive, leaving the adhesive attached to the veneer.

Figure 22:
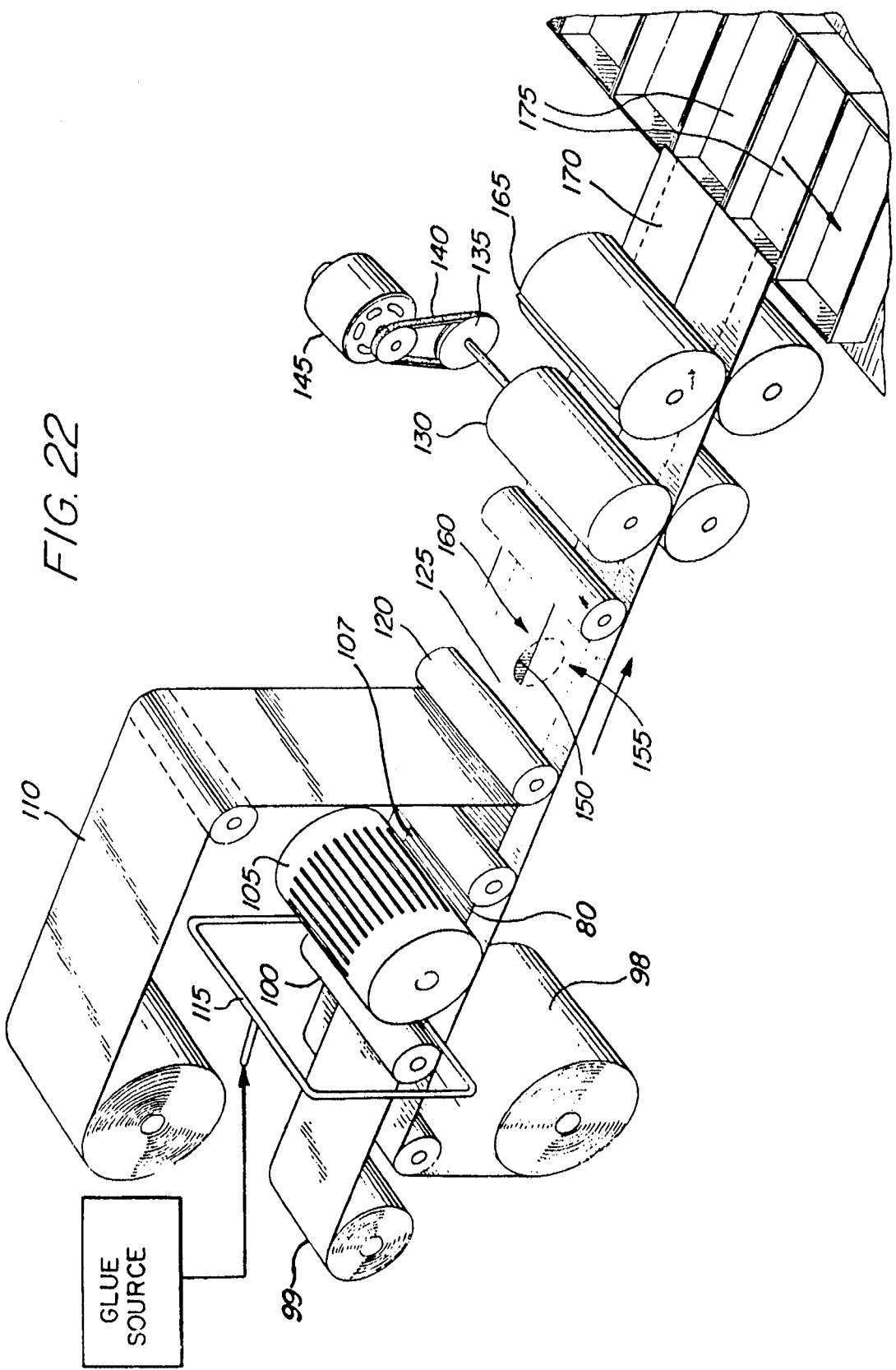
FIG. 22 schematically shows a process for manufacturing the three ply packet containing test ribbons shown in FIG. 5.

The protected test ribbons 80 may be manufactured in any manner, however FIG. 22 shows the preferred process for making the three ply sheets 90 containing the test ribbons 80.

As illustrated, a first protective backing sheet 98 is continuously fed, such as from a roll, onto a continuously fed test ribbon sheet 99. The protective backing sheet 98 is attached to the test ribbon sheet 99 by the use of adhesive 115 applied down the edges of the protective backing sheet.

Preferably the adhesive is laid in an area about 0.5 inch wide along each edge. The test ribbon sheet 99 has a width somewhat shorter than the protective cover sheets, and so the adhesive 115 which is applied only contacts approximately 1–2 mm of each lateral edge of the test ribbon sheet 99. A roller 100 may be used to press the protective backing sheet 98 and the testing ribbon sheet 99 together so that the adhesive bonds adequately.

A cutter 105 sections the test ribbon sheet 99 into individual test ribbons 80. This cutter 105 cuts the test ribbon sheet 99 perpendicular to the longitudinal axis of the sheet. The cutter 105 is of the variety that cuts with a precise downward stroke such that only the test ribbon sheet 99 and not the underlying protective backing sheet 98 is cut. The cutter 105 cuts the test ribbon sheet 99 laterally completely from edge to edge. In this manner, all of the testing ribbons 80 are separated from each other, and yet all adhere to the protective backing sheet 98.

A second protective covering sheet 110, which is made preferably of clear plastic, is then continuously delivered onto the other side of the now cut test ribbon sheet 99. The adhesive 115 which was applied to the first protective backing sheet 98 is used to adhere this protective covering sheet 110. A roller 120 is again used to press the protective covering sheet 110 securely onto this adhesive. Once this second protective covering sheet 110 is attached, the combination is a three-ply sheet 125, where there is a protective covering sheet 110 on the top, a protective backing sheet 98 on the bottom, and test ribbons 80 interposed in between.

All three sheets are preferably fed by a roller 130, or sets thereof, which is rotated by a pulley 135 connected to a belt 140 run by a motor 145. It is contemplated that the feeding mechanism may be of any variety, which are well known to those skilled in the art.

A slicer 150, preferably in the form of a rotating blade, then bisects the three-ply sheet 125 into two three-ply sheets 155, 160 along its centerline. The two three-ply sheets 155, 160 mirror each other. These three-ply sheets 155, 160 therefore have an open longitudinal side which facilitates access to the test ribbons 80, and a closed side where the protective sheets 90, 110 and test ribbons 80 are all attached along a common edge with the applied adhesive strip 115.

A cutter 165 laterally sections the two three-ply sheets 155, 160 into packets 170 of pre-cut protected test ribbons 80. The number of pre-cut test ribbons 80 contained in each packet may vary depending on marketing and consumer needs. Ten to one hundred of the test ribbons 80 are anticipated in each packet 170. These packets 170 are then loaded into containers 175 for shipment and use.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A dental combination, comprising:

a tooth restoration object;

a quantity of adhesive applied to a surface of said object in softened condition; and a tool for positioning said object, said tool having a tip embedded in said adhesive with the adhesive enclosing most of the tip said tip being substantially spherical and rotatable within a socket formed by said adhesive surrounding the tip.

2. The combination of claim 1, wherein said adhesive, when solidified, is sufficiently resilient such that said tool tip can be withdrawn from said socket with either a prying action or with sufficient force pulling away from said element.

3. A dental combination, comprising:

a tooth restoration object;

a quantity of adhesive applied to a surface of said object in softened condition; and a tool having a tip embedded in said adhesive, said tip being coated with a material that will facilitate the release of said tool tip from said adhesive.

4. The combination of claim 3, wherein said material comprises a coating of Teflon.

5. The combination of claim 3, wherein said material comprises a coating of lubricant.

6. A dental combination, comprising:

a tooth restoration object;

a socket of hardened, thermoplastic adhesive material bonded to said object; and a dental tool having a small tip in said socket, said socket and said tip having characteristics such that the tip is movable within the socket so that the object can be positioned in a selected orientation with respect to said tool, and said socket will grip said tip so that the object will remain in the selected position, said socket and said tip having the further characteristic that the tip can be repeatedly inserted and removed from said socket.

7. The combination of claim 6, wherein said tip was embedded in said thermoplastic adhesive when it was in a softened condition; and a release material on said tip that will facilitate the breaking of a bond between the tool tip and the adhesive after the adhesive has hardened.

8. The tool of claim 7, wherein said release material comprises a Teflon coating.

9. The tool of claim 8, wherein said coating is between a thousand and two thousandths of an inch thick.

10. The tool of claim 7, wherein the release material comprises a lubricant.

* * * * *